United States Patent [19]

Takahashi et al.

[11] 3,969,362

[45] *July 13, 1976

[54] ISOPROPYL-N-(5-BROMO OR CHLOROPYRIDYL-2)CARBAMATE

[75] Inventors: Ryohei Takahashi; Isao Yokomichi; Itaru Shigehara; Terumasa Komyoji, all of Kusatsu, Japan

[73] Assignee: Ishihara Sangyo Kaisha Ltd., Osaka, Japan

[ * ] Notice: The portion of the term of this patent subsequent to Oct. 21, 1992, has been disclaimed.

[22] Filed: Apr. 28, 1975

[21] Appl. No.: 572,288

Related U.S. Application Data

[63] Continuation-in-part of Ser. No. 448,205, March 5, 1974, Pat. No. 3,914,240.

[52] U.S. Cl. .......................... 260/295 CA; 424/263
[51] Int. Cl.² ....................................... C07D 213/42
[58] Field of Search ............ 260/295 CA, 295.5 C, 260/294.8 E

[56] References Cited
UNITED STATES PATENTS 3,284,460  11/1966  Wilbert et al. ............... 260/294.8 E
3,284,461  11/1966  Wilbert et al. ............... 260/295 CA
3,364,225  1/1968  Wilbert et al. ............... 260/295 CA

OTHER PUBLICATIONS

Shriner et al., J. Am. Chem. Soc., vol. 74, pp. 549–550, Jan. 20, 1952.

Shaw et al., Chem. Abstracts, vol. 47 (21), pp. 11,638b–11,638h, Nov. 10, 1953.

*Primary Examiner*—Alan L. Rotman
*Attorney, Agent, or Firm*—Oblon, Fisher, Spivak, McClelland & Maier

[57] ABSTRACT

Compounds of the formula:

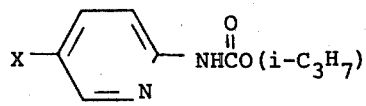

wherein X represents chlorine or bromine have been found to be effective fungicides.

3 Claims, No Drawings

ISOPROPYL-N-(5-BROMO OR CHLOROPYRIDYL-2)CARBAMATE

CROSS-REFERENCE TO RELATED APPLICATIONS

This application is a continuation-in-part of application Ser. No. 448,205, filed Mar. 5, 1974, now U.S. Pat. No. 3,914,240.

BACKGROUND OF THE INVENTION

1. Field of the Invention

This invention relates to an agricultural fungicide which effectively inhibits fungi diseases in plants.

2. Description of the Prior Art

Various agricultural fungicides are known for preventing diseases in agricultural plants, however, there is a continuing search for fungicides which are more effective than prior art materials, or which are effective for specific utilities. The fungicidal effects of n-propyl-N-(5-chloropyridyl-2) carbamate and other n-propyl-N-halopyridyl carbamates have been tested. However, desirable agricultural fungicidal effects were not demonstrated.

SUMMARY OF THE INVENTION

It is one object of this invention to provide an agricultural fungicide for inhibiting various toxic germs, such as *Piricularia oryzae, Pellicularia sasakki, Rhizoctonia solani, Corticium rolfsii*, especially Rhizoctonia bacteria, without chemical injury (phytotoxicity). It is another object sasakii, of the invention to provide an agricultural fungicide which is superior to the known agricultural fungicides, e.g., commercial pentachloronitrobenzene.

These and other objects of this invention as will hereinafter become more readily apparent from the following description have been attained by the discovery of the fungicidal effects of a compound having the formula:

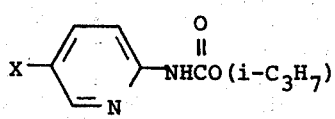

Wherein X represents chlorine or bromine.

DETAILED DESCRIPTION OF THE PREFERRED EMBODIMENTS

The agricultural fungicides of this invention can be prepared by the following reactions:

wherein X is defined as above. The reaction steps (1) and (3) are performed at reflux temperature, e.g., 50°–150°C for 0.5 – 3 hours, preferably about 1 hour, in a solvent, such as benzene, dioxane, xylene, toluene or the like.

The halogenation step (2) is performed at 10°–50°C, preferably 20°–30°C, by introducing chlorine or bromine gas into a solvent such a acetic acid, chloroform, etc.

Having generally described the invention, a more complete understanding can be obtained by reference to certain specific examples, which are included for purposes of illustration only and are not intended to be limiting unless otherwise specified.

The following is a typical example of the preparations of the pyridylcarbamate compounds according to the invention.

EXAMPLE

Preparation of isopropyl N-(5-chloropyridyl-2)carbamate

A 3 liter four-necked flask equipped with a stirrer, a thermometer, a dropping funnel and a condenser, was charged with 260 g (2.12 mole) of isopropyl-chloroformate and 500 ml of benzene. The temperature of the mixture was kept at 10° – 20°C and a solution of 100 g (1.06 mole) of 2-aminopyridine in benzene was added dropwise to the mixture with stirring. The reaction mixture was kept at room temperature for 1.5 hours with stirring and was refluxed for 1 hour. The reaction mixture was cooled to room temperature and filtered. The filtrate was concentraated to obtain crystals. After recrystallization, 87 g (0.925 mole) of the crystals were dissolved in acetic acid and chlorine gas was introduced at 25°–30°C for 3 hours with stirring. After the reaction, the reaction mixture was poured into 1 liter of cold water and aqueous sodium hydroxide was added to adjust the pH to greater than 9 which caused precipitation of crystals.

The crystals were recrystallized from isobutylalcohol to obtain 47.7 g of isopropyl N-(5-chloropyridyl-2)carbamate, melting point 141° – 143°C.

The pyridylcarbamate compounds of the present invention, i.e., isopropyl-N-(5-chloropyridyl-2)carbamate (C-3) and isopropyl-N-(5-bromopyridyl-2)carbamate (C-5) are characterized by melting points of 141° – 143°C and 142° – 146°C, respectively.

FUNGICIDAL TEST 1

Agar medium containing a specific amount of predetermined concentration of an active ingredient (C-3)

(a) 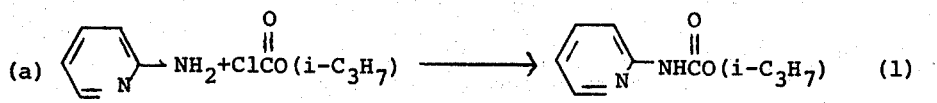

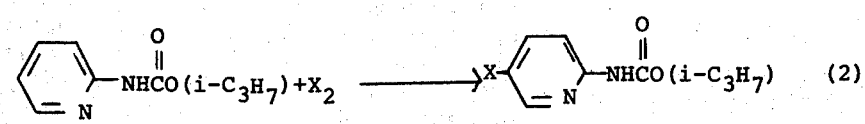

(b) 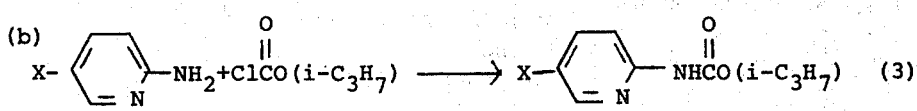

was placed in petri dishes 9 cm in diameter. *Piricularia oryzae, Pellicularia sasakii* or *Rhizoctonia salani* was inoculated into each medium, cultured at 28° – 30°C for 2 days, and the growth condition of fungi in each Petri dish was observed. The growth of *Piricularia oryzae* or *Pellicularia sasakii* was inhibited at the active ingredient concentration of 6.25 ppm. The growth of *Rhizoctonia solani* was inhibited at 12.5 ppm.

FUNGICIDAL TEST 2

Porcelain pots 9 cm in diameter were filled with a suitable amount of upland soil and 5 cucumber seeds (grade Hannichi Fushinari) were sowed in each.

Into each pot 1 g of powdered bran in which *Rhizoctona solani* was grown was inoculated 2 days after sowing. An aqueous dispersion (20 ml) of a specific concentration of an active ingredient was poured into each pot, and water was poured in at a desirable time. The numbers of cucumber buds, seedlings and normally grown seedlings were observed 6 days after inoculation, and the rates of the buds, seedlings, and normally grown seedlings were measured.

The results are shown in Table 1.

TABLE 1

| Active ingredient | (Active ingredient 500 ppm) Growth degree of plant (%) | | |
|---|---|---|---|
| | Sprouting rate (germination rate) | Seedling rate | Normally grown seedling rate |
| C-3 | 90 | 90 | 90 |
| C-5 | 90 | 90 | 80 |
| Ref. 1 | 4 | 0 | 0 |
| Ref. 2 | 2 | 2 | 0 |
| Non-treated | 0 | 0 | 0 |

Ref. 1 : n-propyl N-(5-chloropyridyl-2)carbamate
Ref. 2 : n-propyl N-(5-bromopyridyl-2)carbamate

FUNGICIDAL TEST 3

Fungicidal Test 2 was repeated using lower concentrations of the active ingredients.

The results are shown in Table 2.

TABLE 2

| Active Ingredient | (Active Ingredient 62.5 ppm) Growth degree of plant (%) | | |
|---|---|---|---|
| | Sprouting rate (germination rate) | Seedling rate | Normally grown seedling rate |
| C-3 | 80 | 80 | 80 |
| C-5 | 80 | 70 | 60 |
| ethyl (5-chloropyridyl-2)-carbamate | 30 | 20 | 0 |
| PCNB | 60 | 20 | 10 |
| Non-treated | 0 | 0 | 0 |

Note:
PCNB : pentachloronitrobenzene

FUNGICIDAL TEST 4

Fungicidal Test 2 was repeated except that the time of application of the active ingredient was changed and the growth degree of the plant was observed 4 days after the inoculation of the fungi. The results are shown in Table 3.

TABLE 3

| Active Ingredient | (Active Ingredient 500 ppm) Growth degree of plant (%) Inoculation was made the following days of treatment | | | |
|---|---|---|---|---|
| | 1 day | 3 days | 5 days | 7 days |
| C-3 | *1 100 | 100 | 100 | 100 |
| | *2 100 | 90 | 80 | 100 |
| | *3 90 | 90 | 60 | 80 |
| PCNB | *1 90 | 70 | 60 | 60 |
| | *2 80 | 40 | 20 | 40 |
| | *3 80 | 30 | 0 | 30 |

*1: sprouting rate (germination rate)
*2: seedling rate
*3: normally grown seedling rate

FUNGICIDAL TEST 5

A 1/900 Are pot made of plastic, was filled with a suitable amount of soil. Cucumber, rice, adzuki bean (Japanese), cotton, kidney, bean, beet, radish, and tomato seeds were sowed and 300 ml of an aqueous dispersion of the active ingredient (C-3) having a concentration of 2000 ppm was added. A solution having a concentration of active ingredient of 1000 ppm was poured into each pot on the next day; at suitable times, water was poured into each pot. The growth degree of the plants was observed 12 days and 21 days after the application of the active ingredient. No chemical injury (phytotoxicity) was found.

As is clear from the fungicidal test results, the compounds of this invention impart an excellent fungicidal effect to various fungi which cause plant diseases, without chemical injury (phytotoxicity), in concentrations lower than those required by conventional fungicides. Moreover, the duration of the fungicidal effect is excellent, so that the compounds are desirable as agricultural fungicides. When the active ingredients are applied to plants such as cereals, beans, vegetables, fruits, or the like, which are infected, or may be infected, by a toxic fungi, the active ingredients will impart an excellent fungicidal effect, especially to *Piricularia oryzae, Pellicularia sasakii, Rhizoctonia solani* and *Corticium rolfsii*. The inhibition activity of the compounds of this invention as to *Rhizoctonia solani* is very high.

The active ingredient can be used alone or in admixture with an inert carrier, such as talc, kaolin, bentonite, diatomaceous earth, starch, or the like, in a diluted mixture with a liquid diluent, such as water, alcohol, acetone, benzene, or the like. The fungicidal compounds of this invention can be used in the form of an emulsion, dispersion, or wettable powder, by adding a suitable emulsifier, a dispersing agent, an extending agent, or the like. It is also possible to combine these compounds with other fungicides, insecticides, plant growth controlling agents or herbicides to provide synergistic results in some instance. The composition containing the active agent is preferably applied to the seeds before sowing. When the composition in the form of a powder is applied to the seeds, the concentration of the active agent is preferably 10 – 30 weight %. The concentration of the active ingredient in any given utility will depend, of course, upon the form of composition, the time of application, the type of toxic fungi, etc. and is usually 100 – 2000 ppm, preferably 200 – 1000 ppm in liquid form.

| Preparation: | |
|---|---|
| Isopropyl N-(5-chloropyridyl-2)carbamate | 20 wt parts |
| Zeeklite (finely divided clay | 72 wt parts |
| Sodium ligninsulfonate | 8 wt parts |

The three components were uniformly mixed to prepare a wettable agent.

Having now fully described the invention, it will be apparent to one of ordinary skill in the art that many changes and modifications can be made thereto without departing from the spirit or scope of the invention as set forth herein.

What is claimed as new and intended to be covered by letters patent is:

1. An agricultural fungicide of the formula:

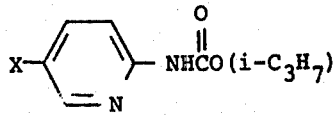

wherein X represents chlorine or bromine.

2. The fungicide of claim 1, which is isopropyl-N-(5-chloropyridyl-2)carbamate.

3. The fungicide of claim 1, which is isopropyl-N-(5-bromopyridyl-2)carbamate.

* * * * *